United States Patent [19]

Gibson et al.

[11] Patent Number: 5,331,098

[45] Date of Patent: Jul. 19, 1994

[54] MONO- AND DI(FUNCTIONALLY-SUBSTITUTED PHENYLENE) SEMI-RIGID CROWNS AND PRECURSORS THEREOF

[75] Inventors: Harry W. Gibson; Yadollah Delaviz, both of Blacksburg, Va.

[73] Assignee: Virginia Tech Intellectual Properties, Inc., Blacksburg, Va.

[21] Appl. No.: 902,185

[22] Filed: Jun. 22, 1992

Related U.S. Application Data

[60] Division of Ser. No. 574,633, Aug. 29, 1990, Pat. No. 5,142,068, which is a continuation-in-part of Ser. No. 418,362, Oct. 6, 1989, Pat. No. 5,028,721.

[51] Int. Cl.$^5$ ............................................. C07D 323/00
[52] U.S. Cl. .................................................... 549/349
[58] Field of Search .......................................... 549/349

[56] References Cited

U.S. PATENT DOCUMENTS

| | | | |
|---|---|---|---|
| 4,876,367 | 10/1989 | Urban | 549/349 |
| 4,935,442 | 6/1990 | Urban | 549/349 |
| 5,082,955 | 1/1992 | Lemaire et al. | 549/349 |

FOREIGN PATENT DOCUMENTS 0726096 4/1980 U.S.S.R.

OTHER PUBLICATIONS

E. Chapoteau et al., "Synthesis, Structures, and Complexing Abilities of Corands Based on 2-Methoxyresorcinol", J. Org. Chem. 1989, 54, 861–867.
M. J. Gunter et al., "A Porphyrin-Based Crown Ether Co-Receptor for the Complexation of Paraquat", Tetrahedron Letters, vol. 31, No. 33, pp. 4801–4804 (1990).
B. L. Allwood et al., "Complexation of Diquat by a Bisparaphenylene-34-Crown-10 Derivative", J. Chem. Soc., Chem. Commun., 1987, pp. 1061–1064.
B. L. Allwood et al., "A Comparison of the Receptor Stereochemistry in [Pt(bipy)(NH$_3$)$_2$. Dinaphtho-30-crown-10][PF$_6$]$_2$ and [Diquat.Dinaphtho-30-crown-10][PF$_6$]$_2$(bipy=2,2'-bipyridine)", J. Chem. Soc., Chem. Commun. 1987, pp. 1054–1058.
B. L. Allwood et al., "Complexation of Paraquat and Diquat by a Bismetaphenylene-32-crown-10 Derivative", J. Chem. Soc., Chem. Commun., 1987, pp. 1058–1061.
S. S. Moore et al., "Host–Guest Complexation. 4. Remote Substituent Effects on Macrocyclic Polyether Binding to Metal and Ammonium Ions", Journal of the American Chemical Society, 99:19, Sep. 14, 1977, pp. 6398–6405.

*Primary Examiner*—C. Warren Ivy
*Assistant Examiner*—Amelia A. Owens
*Attorney, Agent, or Firm*—Richard P. Fennelly; Louis A. Morris

[57] ABSTRACT

Bis(carboalkoxy-substituted m-phenylene)-32-crown-10 compounds, useful as polymerizable monomers, can be formed in one step by reacting a functionalized dihydroxy aromatic compound with a dihalopolyether. In the same reaction, carboalkoxy-substituted m-phenylene-16-crown-5 is formed. Other mono- and di-functionalized bis(phenylene) crown ethers can be made by one step as well as multistep synthesis from similar starting materials.

9 Claims, No Drawings

MONO- AND DI(FUNCTIONALLY-SUBSTITUTED PHENYLENE) SEMI-RIGID CROWNS AND PRECURSORS THEREOF

This is a division of application Ser. No. 07/574,633 filed Aug. 29, 1990 now U.S. Pat. No. 5,142,068 which is in turn a continuation in part of Ser. No. 07/418,362 filed Oct. 6, 1989 and now U.S. Pat. No. 5,028,731.

BACKGROUND OF THE INVENTION

It has recently been suggested that a family of polymeric analogs to macromolecules, termed "polyrotoxanes", be synthesized using crown ethers (or macrocyclic polyethers) as the cyclic component thereof. See H. W. Gibson et al., Polymer Preprints, 1988, 29(1) 248-249 and P. R. Lecavalier et al., Polymer Preprints, 1989, 30(1) 189-190, Ibid., 1990, 31(2), 659-660.

It is known to form hetero crown ethers (also termed "corands") comprising oxygen atoms separated by $(CH_2)_n$ groups and groups of the ortho-phenylene type. See C. J. Pedersen, J. Am. Chem. Soc. 89 (1967) 2495 and 7017. It is well known that such crown ethers can be used as complexation agents.

Chapoteau et al., in J. Org. Chem. 1989, 54, 861-867 mention that crown ethers (corands) based on the 1,3-xylyl subunit have been synthesized with a variety of intraannular or inward facing groups including methoxyl, phenolic, carboxyl, methoxycarbonyl, hydroxyl, nitrile and sulfones.

Moore et al. in J. Amer. Chem. Soc. 99:19, 6398-6410 (1977) show certain monobenzo-crown ethers containing outwardly facing substituents such as $-CH_2C_2H_5$ and $-CN$.

Allwood et al., in a series of reports in J. Chem. Soc., Chem. Commun., 1987, 1054-1064 illustrate a dinaphtho-crown ether (DN30C10 on pp. 1054-1058), a non-substituted bismetaphenylene-32-crown-10 derivative (BMP32C10) on pp. 1058-1061, and a bisparaphenylene-34-crown-10 derivative (BPP34C10) on pp. 1061-1064. The BMP32C10 derivative was synthesized by partial benzylation of resorcinol to yield 3-benzyloxyphenol which was reacted with tetraethylene glycol bis(toluene-p-sulfonate) (TEGBT) to yield 1,11-bis(3'-benzyloxyphenoxy)-36,9-trioxaundecane. Deprotection of that product followed by reaction of the derived diphenol with TEGBT afforded the BMP32C10 derivative. Allwood et al. discuss the ability of BMP32C10 and BPP34C10 to complex such materials as paraquat and diquat.

DESCRIPTION OF THE INVENTION

The present invention, in one embodiment, relates to a novel class of "functionalized" mono- and bis-phenylene-crown ether compounds, e.g., those which may be broadly considered to be bis(extraannular functionalized substituted phenylene) crown ethers, for example, bis(carboalkoxy-substituted phenylene) 32-crown-10 compounds. The term "functionalized" as used herein is intended to cover substituents on the bis-or diphenylene moieties that are outwardly facing or "extraannular" so as to be capable of reaction with other monomeric compounds to form polymers, such as polyesters, polyamides, polyimides and the like. Examples of such substituents include $-COOH$, $-COCl$, $-OH$, $-R-OH$ (where R is alkylene or arylene), $-NH_2$, $-R-NH_2$ (where R is alkylene or arylene) $-SH$, vinyl, or substituted vinyl. The instant invention also relates to precursors for making the "functionalized" mono- or diphenylene-crown ether compounds described above as well as processes for making the functionalized crowns and precursors.

The precursor compounds of the present invention when difunctionalized compounds are ultimately desired have the following formula:

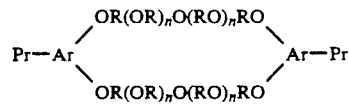

where Pr denotes the precursor group, e.g., lower alkyl, such as methyl, Ar denotes a phenylene ring, R is alkylene, e.g., ethylene, and n is an integer from 1 to 8. When n is one and R is ethylene, a 32-crown-10 structure is realized. The monoprecursors have the same formula depicted above with one precursor group (Pr) not present.

The precursor compound, e.g., Pr=R (e.g., methyl), $-OR$ (e.g., $-OCH_3$), X, $-SR$, $-NO_2$, or $-NR_2$, can be synthesized by the following four-step procedure, if desired. In this procedure, Pr is methyl. The first step involves the reaction of a precursor-substituted dihydroxy aromatic compound, e.g., 3,5-dihydroxytoluene (also termed "orcinol monohydrate") with a halopolyether (e.g., chloropolyether) containing a hydroxy protecting group, such as tetrahydropyranyl, on one end thereof to form an initial reaction product:

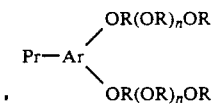

where Pr denotes the precursor group, $R_1$ is the hydroxy protecting group, Ar denotes the phenylene ring, and $-OR(OR)_nOP$ is derived from the halopolyether with R being alkylene (e.g., ethylene), and n being from 1 to 8. The reaction conditions can be as follows: sodium hydroxide as base, 1-butanol as solvent at reflux for thirty hours.

The reaction product is then acid-catalyzed deprotected under inert gas (e.g., nitrogen) to form the corresponding diol upon removal of the protective group P.

The resulting diol is then reacted with tosyl halide (e.g., tosyl chloride) using an amine acid acceptor in order to form the corresponding tosylate.

The cyclization reaction to form the precursor to the final crown ether product is accomplished by reacting the foregoing tosylate with the previously described diol, e.g., (or an analogous diol with n being of a different value) in the presence of an appropriate solvent (e.g., tetrahydrofuran). The final product can be envisioned as having the formula:

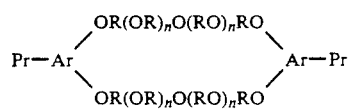

where Pr, Ar, R, and n are as described above. In the case of a 32-crown-10 product, n will be equal to 1 and R is ethylene.

The aforementioned precursor crown, containing a lower alkyl precursor moiety (Pr), such as methyl, can be converted to certain of the functionalized crown ether compounds to be described below by appropriately converting the alkyl group into a functional group capable of polymerization. For example, a carboxylic acid functional group is derivable by oxidizing the alkyl precursor moiety Pr using conventional oxidants, such as potassium permanganate. Once the carboxylic acid functional group is obtained, it can be converted, if desired, to alkylenehydroxy (e.g., —CH$_2$OH) by appropriate reduction, e.g., using hydride reducing agents or it can be converted to —C(O)X, X being halo, such as chlorine, by using a suitable halogenating agent, e.g., sulfonyl chloride or phosphorus trichloride.

A one-step process for forming the aforementioned type of precursor crown ether product has also been developed in which the aforementioned precursor-substituted dihydroxy aromatic compound (e.g., orcinol monohydrate) previously described for use in the four-step method is reacted with a poly(alkylene glycol) ditosylate of the general formula Ts(OR)$_n$OTs, where Ts is tosylate, R is alkylene, e.g., ethylene, and n is an integer from 1 to 12. This reaction is preferably carried out in organic solvent (e.g., dioxane plus 1-butanol) under reflux using base (e.g., sodium hydroxide). A novel 16-membered crown ether by-product, also useful as a complexation agent, produced by the one-step process is 5-methyl-(1,3-phenylene) 16-crown-5. Such monofunctional mono-phenylene crown ethers can also be converted by methods similar to those noted above to polymerizable monomers, e.g., by incorporation of vinyl groups or conversion to derivative diols or diacids. The vinyl monomer types will produce polymers with pendant crown ethers which are also suitable for complexation and membrane applications.

The process used herein is one in which a functionalized dihydroxy aromatic compound is reacted with a halopolyether (e.g., a chloropolyether) containing a hydroxy protecting group at one end thereof, such as tetrahydropyranyl to form an initial reaction product:

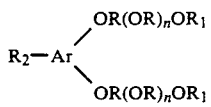

where $R_2$ denotes the functional group, Ar denotes the phenylene ring, and —OR(OR)$_n$OP is derived from the halopolyether with R being alkylene (e.g., ethylene), n being from 1 to 8, and $R_1$ being the protective group. The reaction conditions can be as follows: sodium hydride (NaH) as base, dimethylformamide as solvent at 25° C. to 100° C. for up to five days under an inert gas (e.g., nitrogen).

The reaction product is then acid-catalysis deprotected under inert gas (e.g., nitrogen) to form the corresponding diol upon removal of the protective group $R_1$.

The resulting diol is then reacted with tosyl halide (e.g., tosyl chloride) using an amine acid acceptor in order to form the corresponding tosylate.

The cyclization reaction to form the final crown ether product is accomplished by reacting the foregoing tosylate with the previously described diol, e.g., (or an analogous diol with n being of a different value) in the presence of an alkali metal hydride in an appropriate solvent (e.g., tetrahydrofuran). The final product can be envisioned as having the formula:

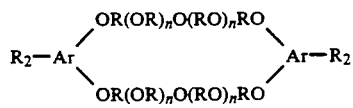

where $R_2$, Ar, R, and n are as described above. In the case of a 32-crown-10 product, n will be equal to 1 and R is ethylene.

While the foregoing discussion illustrated the preparation of crown ethers where oxygen atoms constitute the hetero atoms it is to be understood that one or more of such oxygen atoms can be replaced, for example, with nitrogen to form aza crown compounds.

The instant invention is illustrated by the Examples which follow.

EXPERIMENTAL

General comments. All melting points were taken in capillary tubes with a Haake Buchler melting point apparatus and have been corrected. $^1$H and $^{13}$C NMR spectra were obtained at ambient temperature in deuteriochloroform solutions with Me$_4$Si as internal standard ($\delta=0$ ppm) and recorded on a Bruker WP high resolution spectrometer operating at 270 MHz. Infrared spectra were recorded on a Nicolet MX-1 FTIR spectrometer. Mass spectra were measured with a VGA 7070E Analytical mass spectrometer. Elemental analyses were performed by Atlantic Microlab of Norcross, Ga.

Materials. Unless specified otherwise, reagent grade reactants and solvents were used as received from chemical suppliers. Tetrahydrofuran was refluxed over Na/benzophenone and was used immediately. The tetrahydropyranyl ether of 2-(2'-chloroethoxy)ethanol was prepared by following a literature procedure. (E. P. Kyba et al., J. Am. Chem. Soc. 1977, 99, 2564).

EXAMPLE 1

This illustrates a one-step procedure for forming a bis(carbomethoxy) crown and a novel 16-crown-5 by-product.

Tetraethylene glycol dichloride (13.15 gm, 0.05 mole) in 250 ml dimethylformamide (DMF) was added to 225 ml of DMF containing 9.58 gm (0.05 mole) of methyl 3,5-dihydroxybenzoate and 2.76 gm (0.115 mole) of sodium hydride. The solution was stirred vigorously at 75° C. for twenty-four hours under a blanket of nitrogen, cooled, filtered and evaporated to give a brown viscous oil residue, which was chromatographed on silica gel (7 gm per 1 gm crude products) with diethyl ether as eluent to produce the corand, bis(5-carbomethoxy-1,3-phenylene)-32-crown-10 as a crystalline solid, 2 gm, 11% yield, mp 105.5°–106.5° C., IR (KBr pellet) 1717 (C=O), 1600 (C=C), 1067–1137 (C—O—C) cm$^{-1}$, $^1$H NMR (CDCl$_3$/TMS) $\delta$ 3.6–4.3 (38H, m, OCH$_2$ and OCH$_3$), 6.7 (2H, s, Ph-H$_{-b}$), 7.15 (4H, s, Ph-H$_{-a}$); m/z (EI$^+$): 652 (M$^+$), 621 (M$^+$-OCH$_3$), 590 (M$^+$-2OCH$_3$). Anal. Calcd. for C$_{32}$H$_{44}$O$_{14}$ (MW 652): C, 58.88; H, 6.80. Found: C, 58.67; H, 6.86.

5-carbomethoxy-1,3-phenylene-16-crown-5 was isolated from the above reaction products, 1.59 gm, 9% yield as a needle-like crystalline solid, mp 71°–72° C., $^1$H NMR (CDCl$_3$/TMS) $\delta$ 3.5–4.4 (19H, m, OCH$_2$ and OCH$_3$), 7.2 (2H, s, Ph-H$_{-b}$), 7.35 (1H, s, Ph-H$_{-a}$); m/z (EI+): 326 (M+), 295 (M+-OCH$_3$), 267 (M+-COOCH$_3$), 239 (M+-COOCH$_3$ and CH$_2$CH$_2$). Anal. Calcd. for C$_{16}$H$_{22}$O$_7$ (MW 326): C, 58.89; H, 6.80. Found: C, 58.96; H, 6.83.

EXAMPLE 2

This illustrates the one-step process for forming bis(5-methyl-1,3-phenylene)-32-crown-10 and 1,3-(5-methylphenylene)-16-crown-5.

Tetraethylene glycol ditosylate (50.23 gm, 0.100 mole) in 500 ml dioxane/1-butanol (3:2 v/v) was added to 450 ml of 1-butanol containing orcinol monohydrate (16.40 gm, 0.115 mole) and sodium hydroxide (9.10 gm, 0.230 mole) in 8 ml of water. The solution was refluxed for twenty-four hours, under a blanket of nitrogen, cooled, filtered and evaporated to give a brown viscous oil, which was chromatographed on acidic alumina with ethyl ether to produce bis(5-methyl-1,3-phenylene)-32-crown-10, 2.5 gm, 9% yield (mp and other characteristic data reported below in Example 6) and 1,3-(5-methylphenylene)-16-crown-5 as a needle-like crystalline solid. 1.6 gm, 7% yield, mp 69°-71° C., $^1$H NMR (CDCl$_3$/TMS) δ 2.25 (3H, s, Ph-CH$_3$), 3.60 (4H, t, δ-OCH$_2$), 3.70 (4H, t, δ-OCH$_2$), 3.82 (4H, t, β-OCH$_2$), 4.27 (4H, t, α-OCH$_2$), 6.37 (2H, s, Ph-H$_b$) and 6.92 (1H, s, Ph-H$_a$) for H$_a$ and H$_b$; m/z, (EI+): 282 (M+), 195 (M+-OCH$_2$CH$_2$OCH$_2$CH$_2$), 168 (M+-CH$_2$CH$_2$OCH$_2$CH$_2$OCH$_2$CH$_2$), 151 (M+-OCH$_2$CH$_2$OCH$_2$CH$_2$OCH$_2$CH$_2$), 124 (M+-CH$_2$CH$_2$OCH$_2$CH$_2$OCH$_2$CH$_2$OCH$_2$CH$_2$); Anal. Calcd for C$_{15}$H$_{22}$O$_5$(MW 282): C, 63.81; H, 7.85. Found: C, 63.67; H, 7.86.

EXAMPLE 3

This Example illustrates the first step in the four-step procedure for preparing the precursor crown ether, bis(5-methyl-1,3-phenylene)-32-crown-10.

Following a literature procedure (M. Newcomb et al., J. Am. Chem. Soc. 1977, 99, 6405), a solution of 2-(2'-chloroethoxyethyl) tetrahydropyranyl ether (55.50 gm, 0.266 mole) in 150 ml 1-butanol, containing orcinol monohydrate (11.00 gm, 0.077 mole) and sodium hydroxide (7.50 gm. 0.185 mole). The resulting mixture was refluxed for fifteen hours and an additional amount of sodium hydroxide (2.60 gm, 0.065 mole) was added. After an additional fifteen hours at reflux, sodium chloride (14.0 gm) was filtered from the cooled reaction mixture, which was evaporated. Unreacted tetrahydropyranyl ether was removed by distillation from the residue, to give the compound 3,5-bis(5-tetrahydropyranyloxy-3-oxa-1-pentyloxy)toluene: 33.0 gm, 95%, oil; IR (neat) 1600 (C=C), 1129 (C—O—C) cm$^{-1}$; $^1$H NMR (CDCl$_3$/TMS δ 1.3–1.9 (12H, m, CH$_2$), 2.25 (3H, s, Ph-CH$_3$), 3.5–4.1 (20H, m, OCH$_2$), 4.6 (3H, s, O—CH—O ) and 6.35 (3H, s, Ph-H).

EXAMPLE 4

This illustrates the next step in the synthesis using the product from Example 3.

The above bistetrahydropyranyl ether from Example 5 (33.00 gm. 0.070 mole) was dissolved in 500 ml CH$_3$OH:CH$_2$Cl$_2$ (1:1 v/v) and 5 ml concentrated hydrochloric acid was added. The solution was stirred for 4 hours at room temperature, then neutralized with NaHCO$_3$. The organic layer was separated, dried over magnesium sulfate, filtered and the solvent was removed in vacuo. The residue was distilled to give the diol 3,5-bis(5-hydroxy-3-oxa-1-pentyloxy)toluene: bp 195°–197° C./0.05 mm, 19.2 gm, 92%; IR (neat) 3405 (O—H), 1600 (C=C), 1129 (C—O—C) cm$^{-1}$; $^1$H NMR (CDCl$_3$/TMS) δ 2.25 (3H, s, Ph-H), 2.8 (2H, br, s, OH), 3.5–4.2 (16H, m, OCH$_2$) and 6.35 (3H, s, Ph-H).

EXAMPLE 5

The third step in the four-step synthesis for making bis(5-methyl-1,3-phenylene)-32-crown-10 is described herein.

Literature procedure (M. Ouchi, J. Org. Chem. 1984, 49, 1408) was generally followed. It was modified by using a reaction time of twenty-four hours instead of two hours at 0° C. This allowed for a 97% yield of the ditosylate (literature: 81%) without the necessity of using column chromatography for purification. The excess of p-toluenesulfonyl chloride was removed from the reaction product simply by washing with hexanes.

Separate solutions of the diol from Example 6 (10.00 gm, 0.033 mole) in 37 mmole (6 ml) of dry pyridine and p-toluenesulfonyl chloride (19.25 gm, 0.100 mole) in 77 ml of pyridine were cooled to −20° C. The solutions were then combined and maintained at −20° C. for seventy-four hours while stirring. The reaction mixture was then poured into 240 ml ice water, and this mixture was extracted with three 120 ml volumes of dichloromethane. The combined organic phase was washed with three 170 ml portions of ice cold 6N aqueous HCl and then with 150 ml of saturated aqueous ammonium chloride. After drying of the organic phase over anhydrous magnesium sulfate and filtration, removal of solvent under reduced pressure yielded the ditosylate 3,5-bis(5-toluenesulfonyloxy-3-oxa-1-pentyloxy)toluene: viscous oil, 19 gm, 97%; IR (neat) 1355, 1190 and 1175 (S=O), 1600 (C=C), 1129 (C—O—C) cm$^{-1}$; $^1$H NMR (CDCl$_3$/TMS) δ 2.25 (3H, s, Ph-H), 2.4 (3H, s, O-SO$_2$-Ph-CH$_3$), 3.7–4.3 (16H,m, OCH$_2$), 6.2–6.4 (3H, m, Ph-H), 7.55 (8H, AB, q, O-SO$_2$-Ph-H).

EXAMPLE 6

This illustrates the final step in the four-step synthesis for making bis(5-methyl-1,3-phenylene)-32-crown-10.

To a solution of 3,5-bis(5-hydroxy-3-oxa-1-pentyloxy)toluene (1.50 gm, 5 mole) in 75 ml THF (dried over sodium/benzophenone) was added potassium t-butoxide (1.6 gm, 15 mmole), and the solution was stirred under nitrogen for one hour. A solution of 3,5-bis(5-toluenesulfonyloxy-3-oxa-1-pentyloxy)toluene (3.0 gm, 5 mmole) in 37 ml THF was added, the mixture was stirred at room temperature for five days and then refluxed for thirty-six hours. The solvent was evaporated in vacuo, and the residue was partitioned between 100 ml of CH$_2$Cl$_2$ and 100 ml of water. The organic layer was dried over sodium sulfate and evaporated in vacuo, to give a brown viscous oil, 2.5 gm, which was chromatographed on 75 gm neutral alumina with ethyl acetate-petroleum ether (2:1 v/v) as eluent to produce 0.8 gm, 25% of desired macrocycle as a white solid, mp, 94°-96° C.; IR (KBr) 1129 (C—O—C) cm$^{-1}$; $^1$H NMR (CDCl$_3$/TMS) δ 2.25 (6H, s, Ph-H); 3.7 (16H, s, γ/δ-OCH$_2$), 3.82 (8H, t, β-OCH$_2$), 4.05 (8H, t, α-OCH$_2$), 6.32 (6H, s, Ph-H); m/z (Cl+): 565 (M+ +1), 521 (M+-OCH$_2$CH$_2$); Anal. Calcd for C$_{30}$H$_{44}$O$_{10}$(MW 564): C, 63.81; H, 7.85. Found: C, 63.74; H, 7.86.

EXAMPLE 7

This illustrates the first two steps in the synthesis of 5-methyl-bis(1,3-phenylene)-32-crown-10.

A solution of 34 gm (0.163 mole) 2-(2'-chloroethoxyethyltetrahydropyranyl ether in 75 ml of 1-butanol was added dropwise to a mixture of (5.5 gm, 0.05 mole) of resorcinol and (4.1 gm, 0.1 mole) of NaOH in 150 ml of boiling 1-butanol. The resulting mixture was stirred under reflux for fifteen hours, and an additional 1.5 gm (0.03 mole) of NaOH was added after an additional fifteen hours at reflux. The cooled reaction mixture was filtered from NaCl (11.0 gm) and concentrated in vacuo to remove solvent and low boiling components. A viscous oil (16.5 gm) was obtained. The oily residue was dissolved in 300 ml $CH_3OH:CH_2Cl_2$ (1:1 v/v) and 4 ml concentrated hydrochloric acid was added, the solution was stirred for three hours, neutralized with $NaHCO_3$, and extracted with three portions of 150 ml chloroform. The combined organic phase was dried over magnesium sulfate, the solvent was removed in vacuo, and the residue was distilled to give 1,3-bis(5-hydroxy-3-oxa-1-pentyloxy)benzene: bp 190°–195° C./0.1 mm (mp 36°–38° C.), 12 gm, 91%; IR (neat) 3405 (O—H) 1600 (C=C) 1129 (C—O—C) cm$^{-1}$; $^1$H NMR ($CDCl_3$/TMS) δ 3.35 (2H, s, OH), 3.55–4.3 (16H, m, $OCH_2$), 6.7–7.22 (4H, m, Ph-H).

EXAMPLE 8

This illustrates the final step (cyclization) in the synthesis of 5-methyl-bis(1,3-phenylene)-32-crown-10.

To a solution of 2.86 gm (10 mmole) of the diol from Example 7 in 150 ml tetrahydrofuran (THF) (freshly distilled over sodium/benzophenone) was added 2.8 gm (25 mmole) of t-BuOK, and the solution was stirred under nitrogen for one hour. A solution of 6.0 gm (10 mmole) of the ditosylate from Example 5 in 74 ml THF was added, the mixture was stirred at room temperature for 5 days and then refluxed for thirty-six hours. The solvent was evaporated in vacuo, and the residue was partitioned between 200 ml of $CH_2Cl_2$ and 200 ml water. The organic layer was dried over magnesium sulfate and evaporated in vacuo, to give a brown viscous oil (7.0 gm), which was chromatographed on 200 gm neutral alumina with ethyl acetate petroleum ether (2:1 v/v) as eluent to produce the title macrocycle, 1.1 gm, 20%, as a white crystalline solid, mp 66°–68° C. IR (KBr), 1600 (C=C), 1129 (C—O—C) cm$^{-1}$; $^1$H NMR ($CDCl_3$/TMS) δ 2.25 (3H, s, Ph-$CH_3$), 3.65 (16H, s, γ/δ-$OCH_2$), 3.85 (8H, t, β-$OCH_2$), 4.1 (8H, t, α-$OCH_2$), 6.34 (3H, s, Ph-$H_c$), 6.5 (3H, d, Ph-$H_b$) 7.12 (1H, t, Ph-$H_a$); m/z, (EI+): 550 (M+) 283 (M+-$CH_2CH_2OCH_2CH_2OC_6H_4OCH_2CH_2OCH_2$-$H_2OCH_2$). Anal. Calcd for $C_{29}H_{41}O_{10}$ (MW 550): C, 63.37; H, 7.52. Found: C, 63.17; H, 7.71.

We claim:

1. Bis(extraannular functionally-substituted phenylene)-32-crown-10 compounds which are 5-carboalkoxy substituted.

2. Compounds as claimed in claim 1 wherein the carboalkoxy moiety is carbomethoxy.

3. Extraannular functionally-substituted phenylene-16-crown-5 compounds which are 5-carboalkoxy-1,3-phenylene.

4. Compounds as claimed in claim 3 wherein the carboalkoxy moiety is carbomethoxy.

5. Bis(extraannular alkyl-substituted phenylene)-32-crown-10 compounds which are 5-methyl-1,3-phenylene.

6. 1,3-(5-methylphenylene)-16-crown-5.

7. Extraannular mono- or alkyl-substituted bis(phenylene)-32-crown-10 compounds which are 5-methyl-bis(1,3-phenylene.

8. Extraannular mono-carboalkoxy bis(phenylene)-32-crown-10 compounds which are 5-carboalkoxy bis-(1,3-phenylene).

9. Compounds as claimed in claim 8 where the carboalkoxy is carbomethoxy.

* * * * *